(12) United States Patent
Kim (10) Patent No.: US 11,446,124 B2
(45) Date of Patent: Sep. 20, 2022

(54) IMPLANT SET DEVICE FOR SINUS MEMBRANE ELEVATION

(71) Applicant: TRUABUTMENT KOREA, INC., Bucheon-si (KR)

(72) Inventor: Haeng Oh Kim, Busan (KR)

(73) Assignee: Truabutment Korea, Inc., Bucheon-si (KR)

( * ) Notice: Subject to any disclaimer, the term of this patent is extended or adjusted under 35 U.S.C. 154(b) by 322 days.

(21) Appl. No.: 16/795,470

(22) Filed: Feb. 19, 2020

(65) Prior Publication Data

US 2020/0276000 A1 Sep. 3, 2020

(30) Foreign Application Priority Data

Feb. 28, 2019 (KR) .................. 10-2019-0023853

(51) Int. Cl.
*A61C 8/00* (2006.01)
*A61C 3/04* (2006.01)
*A61B 17/17* (2006.01)
*A61B 17/16* (2006.01)

(52) U.S. Cl.
CPC ........ *A61C 8/0092* (2013.01); *A61B 17/1673* (2013.01); *A61B 17/176* (2013.01); *A61C 3/04* (2013.01)

(58) Field of Classification Search
CPC ......... A61C 8/0092; A61C 3/04; A61C 1/082; A61C 1/084; A61B 17/1673; A61B 17/176
See application file for complete search history.

(56) References Cited

U.S. PATENT DOCUMENTS

| 5,525,314 A  * | 6/1996 | Hurson ................. A61B 50/33 206/379 |
| 2005/0064368 A1* | 3/2005 | Kitamura ............. A61C 8/0092 433/141 |
| 2013/0150857 A1* | 6/2013 | Better ................. A61C 8/0092 606/80 |
| 2016/0128810 A1* | 5/2016 | Fostick ................. A61C 19/04 703/1 |

* cited by examiner

*Primary Examiner* — Heidi M Eide
(74) *Attorney, Agent, or Firm* — McDonnell Boehnen Hulbert & Berghoff LLP (57) ABSTRACT

An implant set device for sinus membrane elevation is provided. Herein, implant set device for sinus membrane elevation includes an initial drill group for an alveolar bone including a multiplicity of initial drills for an alveolar bone, a dilatation drill group for an alveolar bone including a multiplicity of dilatation drills for an alveolar bone, a sinus drill group including a multiplicity of sinus drills, a final drill group including first final drills, and a receiver having a drill region where the drills can be received in a first direction with the effective length increasing in each drill group and the drills can be received in a second direction in which drills of each drill group belonging to the drill group for surgery are arranged in a surgical procedure of the sinus membrane elevation.

9 Claims, 7 Drawing Sheets

IMPLANT SET DEVICE FOR SINUS MEMBRANE ELEVATION

CROSS REFERENCE TO RELATED APPLICATION

The present application claims priority to Korean Patent Application No. 10-2019-0023853, filed Feb. 28, 2019, the entire contents of which is incorporated herein for all purposes by this reference.

BACKGROUND OF THE INVENTION

Field of the Invention

The present invention related to an implant set device for dental implant placement by sinus membrane elevation, and more particularly, to an implant set device for sinus membrane elevation, which is used for drilling an alveolar bone for bone grafting in a maxillary sinus during an implant procedure.

Description of the Related Art

In the past, when a tooth was missing, an artificial crown, bridge, an interlocking partial denture, or a whole denture were used for dental restoration. Recently, due to inconveniences in their use, the application of an implant has been spreading.

An implant is a dental prosthesis that fixes an artificial tooth by placing a fixture on or in the jawbone for the purpose of restoring a missing tooth.

A drilling process for fixture placement is considerably difficult to accurately measure the depth and direction of a procedure, not only for a novice who has not carried out sufficient implant treatments but also for an experienced person.

Particularly, during an implant procedure, when there is not enough bone left to place an implant between the sinus membrane and the alveolar bone of a patient, a sinus membrane elevation is often performed where the sinus membrane tissue located above the alveolar bone is lifted and a space thus made is filled with an artificial bone (bone graft material) in order to secure a sufficient amount of bone for implant placement.

Sinus membrane tissue is a tissue that is formed inside a sinus membrane to regulate the humidity in a nasal cavity and a resonance during vocalization. However, drilling for sinus membrane elevation requires a higher degree of difficulty than drilling for placement of a general fixture in that a through hole should be formed through an alveolar bone to insert an artificial bone but the sinus membrane tissue should not be damaged. For example, when a practitioner has a low skill level or misunderstands an alveolar bone thickness for drilling, if the sinus membrane tissue is damaged, the risk of infection increases in the sinus membrane.

In order to improve the problem, a guide stent fabricated in precise dimensions based on three-dimensional image data of mouth is fixed by being wound around the whole interior of mouth. In such a situation, based on a three-dimensional image, a distance from an alignment reference plane to a sinus membrane tissue is obtained to set an insertion depth of a cutting edge.

In this case, to adjust an insertion depth of a cutting edge, an auxiliary stopper corresponding to the drilling insertion depth is conventionally selected among a plurality of hollow auxiliary stoppers having different lengths and is inserted into an outer circumference surface of a drill guide. Hence, as an outer circumference surface of guide is protruded from a guide hole of a guide stent by the length of an auxiliary stopper, it is not firmly supported by the inner surface of the guide hole.

In other words, in such a supported state, since an outer circumference surface of guide and a guide stent cannot secure sufficient surface contact, the outer circumference surface of guide is not firmly supported by the guide stent during drilling, and the cutting portion of a drill becomes susceptible to vibration or deformation during drilling.

Especially, a cutting portion of a drill should be long enough to use an auxiliary stopper. As the length of a cutting portion with a relatively small diameter is longer, the cutting portion is more susceptible to vibration or deformation in a drilling process. This causes a problem that the cutting portion slightly deviates from an intended drilling position or direction.

In addition, since an outer circumference surface of guide of drill is not sufficiently supported by surface contact with a guide stent, in order to maintain a supported state of drill during a drilling process, a practitioner should keep strongly pressing a drill and an auxiliary stopper towards a guide stent.

In addition, when a patient has a narrow oral cavity structure or a sinus membrane elevation is to be performed for a molar where the gap between upper and lower teeth is narrow, a drill should be inserted in a cutting direction with a long auxiliary stopper being interposed. There is a lot of difficulty in securing a space in the vertical direction.

SUMMARY OF THE INVENTION

The object of the present invention is to provide a drill suitable for a patient's mouth and alveolar bone in an implant surgery including sinus membrane elevation, thereby providing an implant set device for sinus membrane elevation, which prevents sinus membrane tissue from being damaged by a drill.

The objects of the present invention are not limited to the above-mentioned objects, and other objects not mentioned can be clearly understood by those skilled in the art from the following description.

According to one aspect of the present invention, an implant set device for sinus membrane elevation includes an initial drill group for an alveolar bone including a multiplicity of initial drills for an alveolar bone, which consist of a same effective diameter and an effective length increasing at a first interval, a dilatation drill group for an alveolar bone including a multiplicity of dilatation (step) drills for an alveolar bone, which consist of a same effective diameter that is larger than the effective diameter of the initial drills for an alveolar bone and an effective length that increases at a second interval and is equal to the effective length of the initial drills for an alveolar bone, which belong to a drill group for surgery that is set in the sinus membrane elevation, a sinus drill group including a multiplicity of sinus drills, which exposes the sinus and consist of a same effective diameter that is larger than the effective diameter of the dilatation drills for an alveolar bone and an effective length that increases at a third interval and is longer than the effective length of the dilatation drills for an alveolar bone belonging to the drill group for surgery, a final drill group including first ultimate drills that form a hole in a bone graft material between the alveolar bone and the sinus, have a same effective diameter, which is larger than the effective diameter of the sinus drills, and an effective length increasing at a fourth interval, and are allocated in each section of the effective length in the drill group for surgery, and a drill receiver having a drill region where the drills can be received in a first direction with the effective length increasing in each drill group and the drills can be received in a second direction in which drills of each drill group belonging to the drill group for surgery are arranged in a surgical procedure of the sinus membrane elevation.

In another embodiment, a guide stent, in which a guide hole guiding the drill is formed, is additionally included, and the effective length of the drill group may be set according to a length from the top of the guide hole to the membrane of sinus.

In addition, each of the drills in the drill groups includes a cutting portion for forming a placement hole, a guide portion that is coupled to the cutting portion to correspond to the guide hole, an engaging portion that protrudes from the guide portion in the direction of the outer diameter of the drill, and a coupling portion mounted on a handpiece that is coupled to the engaging portion and gives a rotational force to the drill. The effective length specified in the drills is a length adding up the cutting portion and the guide portion. The length and diameter of the guide portion in each of the drills may be set to be the same.

In addition, a guide bushing that can be mounted in the guide hole of the guide stent in surgical procedure of the sinus membrane elevation may be further included. The guide bushing may have a shape that adheres closely to the guide hole and may include a body with a hole guiding the drill, an extending portion having elasticity and protruding outwards from the body, and an engaging portion that is placed at the end of the extending portion and is coupled to the bottom of a guide body of the guide stent adjacent to the guide hole.

In another embodiment, the first interval and the third interval may be set to be the same, the fourth interval may be set to larger than the third interval, and the effective length of the first final drill may be set to be equal or greater than a maximum effective length of the sinus drill belonging to the section.

In another embodiment, the first final drill may comprise a cutting portion that cuts the bone graft material and includes a tip portion of non-cutting portion and a guide portion coupled to the cutting portion. The tip portion as a non-cutting portion may have a flat tip surface and a rounded edge shape around the tip surface and may be machined to be smaller than the effective diameter of the sinus drill. The cutting portion may include a lower lateral cutting edge, which is machined to be larger than the effective diameter of the sinus drill and to be smaller than the effective diameter of the first final drill, an upper lateral cutting edge, which is machined to be the same as the effective diameter of the first final drill, a lower recess that is placed between the lower lateral cutting edge and the upper lateral cutting edge and is machined to be smaller than the diameter of the lower lateral cutting edge, and an upper recess that is placed on the top of the upper lateral cutting edge and is machined to be larger than the diameter of the lower recess. The guide portion may be placed between lateral cutting edges of the cutting portion and may have a curved portion which has a gentler slope on the preceding cutting edge than on the trailing cutting edge in a rotational direction of the first final drill.

In addition, the dilatation drill for an alveolar bone may be equipped with a cutting portion for forming a placement hole, and the cutting portion of the dilatation drill may include a lower cutting edge, which has the same effective diameter as the dilatation drill group for an alveolar bone, and an upper cutting edge of which the effective diameter is larger than the effective diameter of the lower cutting edge and is the same as the effective diameter of the sinus drill.

In another embodiment, the final drill group may further include a second final drill, which has a larger effective diameter than the first final drill and the same effective length as the first final drill, in each section of the effective length in the drill group for surgery. The tip portions of the first and second drills may be machined to have the same diameter.

In another embodiment, a multiplicity of bone graft material inserters infusing a bone graft material between an elevated sinus and an alveolar bone, may be further included, the bone graft material inserters may be provided so that each section from a gum to the sinus membrane has one nozzle length, and the receiver may further include a bone graft material inserter region that may receive the multiplicity of bone graft material inserters.

In another embodiment, the receiver may provide a visually recognizable sign in the second direction, where drills of each drill group are arranged, in order to identify a drill according to the procedure of the sinus membrane elevation, and also provide a visually recognizable sign in the first direction in order to identify an effective diameter of a drill belonging to each drill group.

According to the present invention, in an implant treatment, an implant set device for sinus membrane elevation, which can select a drill suitable for a patient's mouth and alveolar bone, is provided to prevent sinus membrane tissue from being damaged by a drill.

Specific details of other embodiments are included in the following description and drawings.

In the figures, reference numbers refer to the same or equivalent portions of the present invention throughout the several figures of the drawing.

DETAILED DESCRIPTION OF THE INVENTION

Hereinafter, exemplary embodiments of the present invention will be described in detail with reference to the accompanying drawings and the contents described below. However, the present invention is not limited to the embodiments described herein and may be embodied in other forms. Rather, the embodiments introduced herein are provided to ensure that the disclosed subject matter is thorough and complete, and that the scope of the invention will be fully conveyed to those skilled in the art. Like numbers refer to like elements throughout. Meanwhile, the terminology used herein is for the purpose of describing particular embodiments only and is not intended to limit the present invention. In this specification, the singular forms also include the plural unless specifically stated otherwise in the text. As used herein, "comprises" and/or "comprising" specifies the presence of the mentioned shapes, numbers, steps, actions, members and/or elements. It does not exclude the presence or addition of one or more other shapes, numbers, steps, actions, members, elements and/or groups thereof.

Hereinafter, with reference to FIGS. 1 to 11, an implant set device for sinus membrane elevation according to one embodiment of the present invention will be described in detail.

Figure 1:
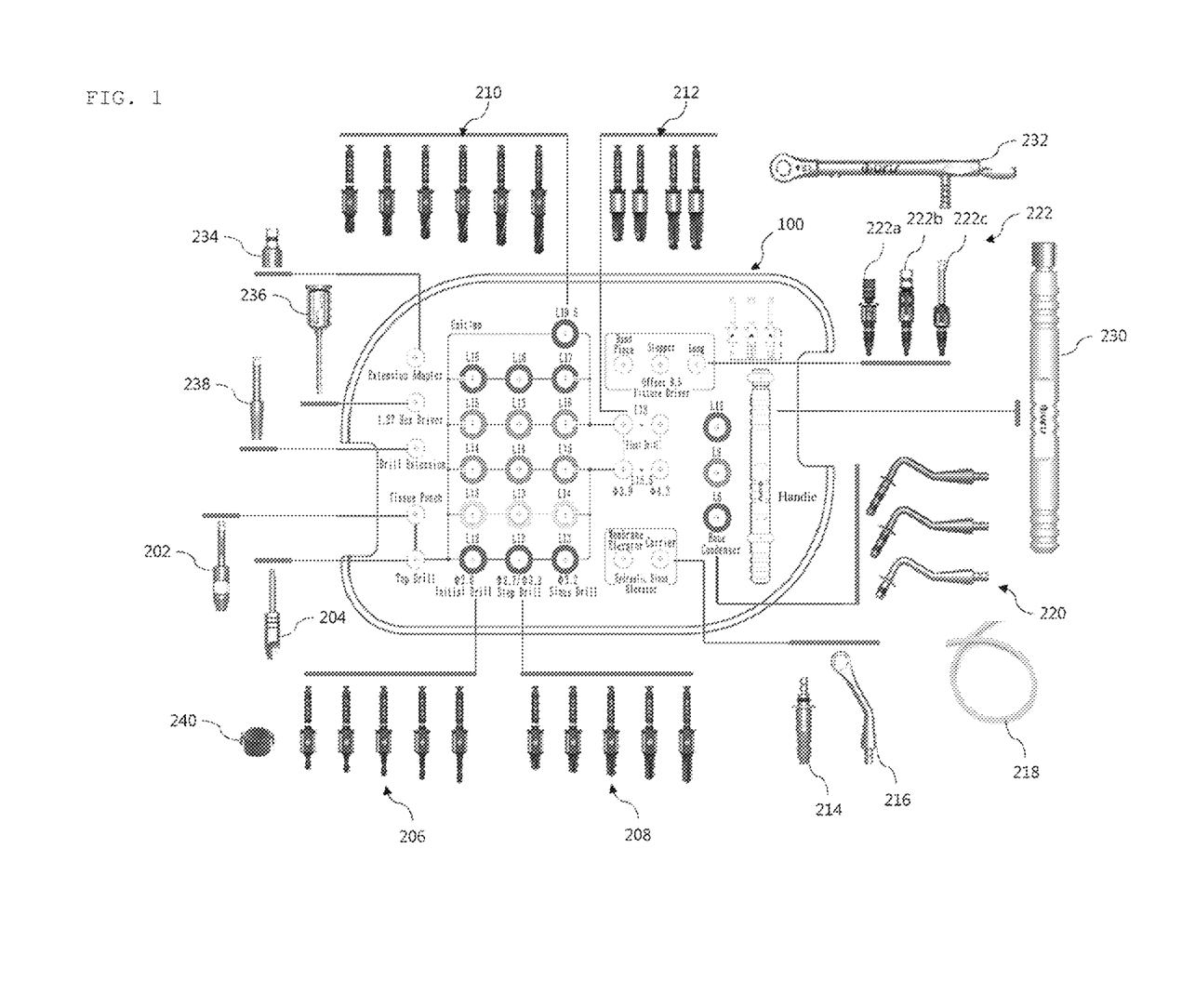
FIG. 1 shows an implant set device for sinus membrane elevation according to an embodiment of the present invention.
Figure 2:
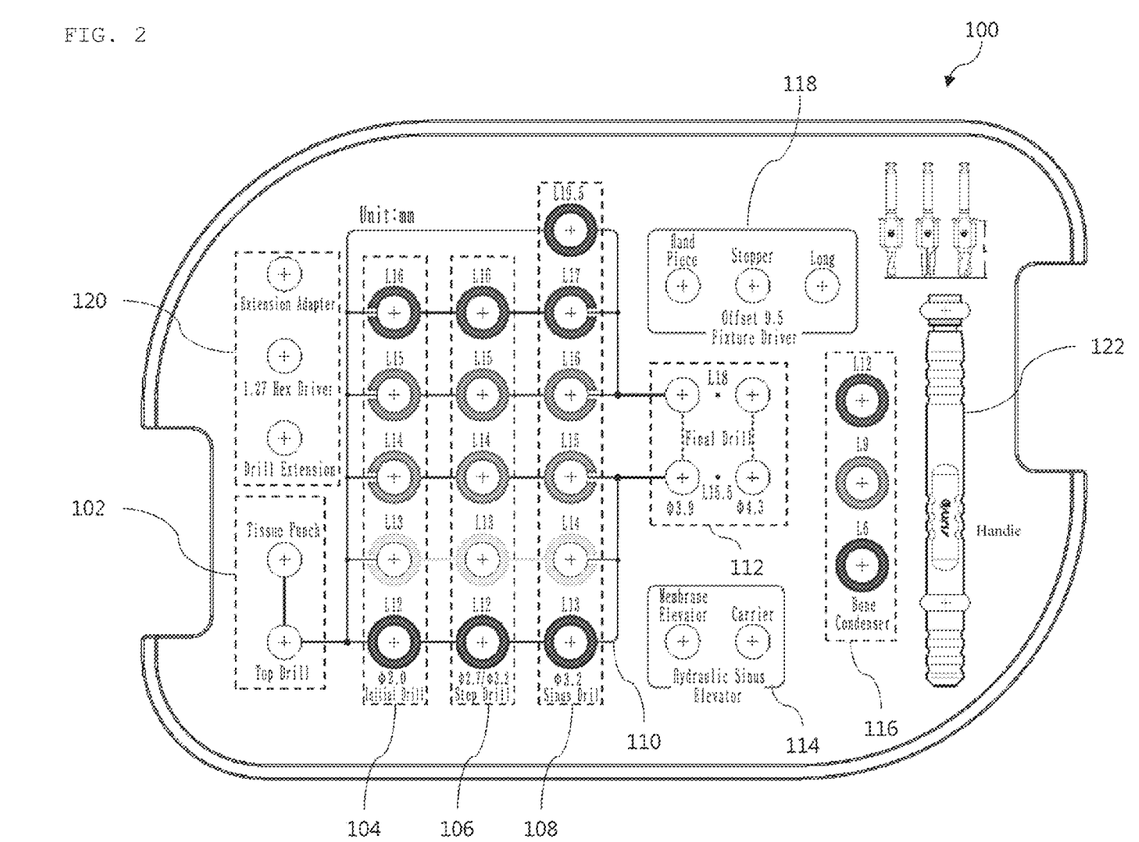
FIG. 2 shows a receiving portion.
Figure 3:
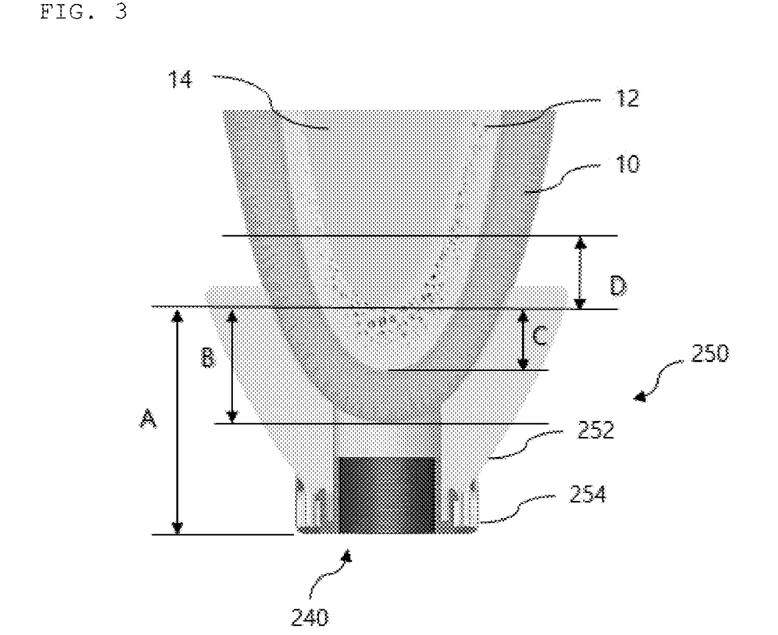
FIG. 3 is a cross-sectional view in which a guide stent equipped with a guide bushing is mounted in gum.

FIG. 1 shows an implant set device for sinus membrane elevation according to an embodiment of the present invention. FIG. 2 shows a receiving portion. FIG. 3 is a cross-sectional view in which a guide stent equipped with a guide bushing is mounted in gum.

Figure 4:
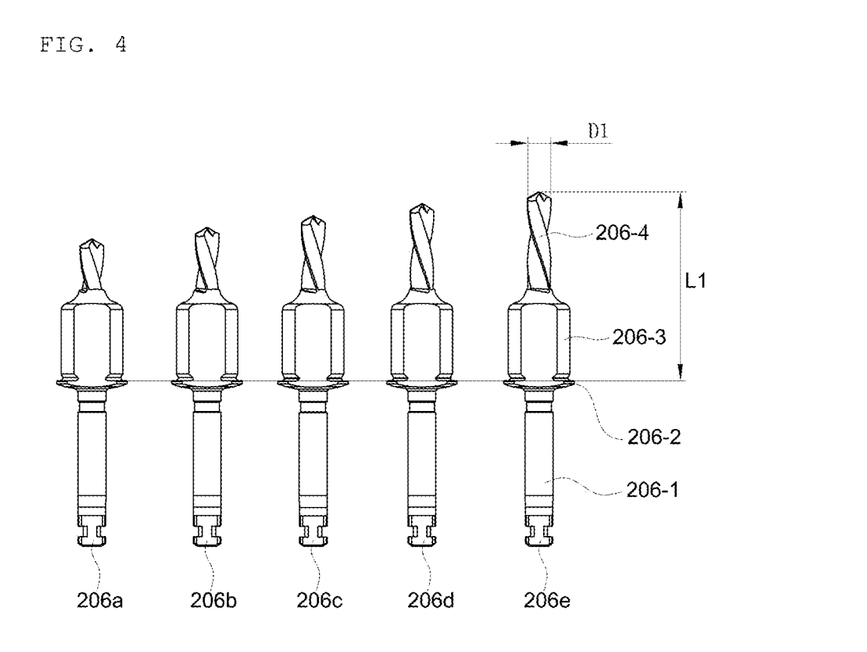
FIG. 4 is a perspective view of initial drills for an alveolar bone, which belong to an initial drill group for an alveolar bone.
Figure 5:
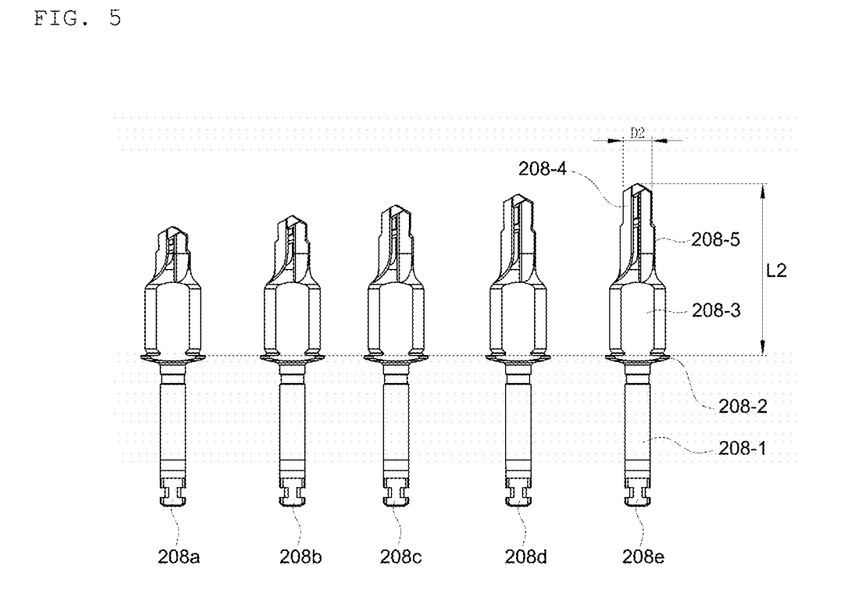
FIG. 5 is a perspective view of dilatation drills for an alveolar bone, which belong to a dilatation drill group for an alveolar bone.
Figure 6:
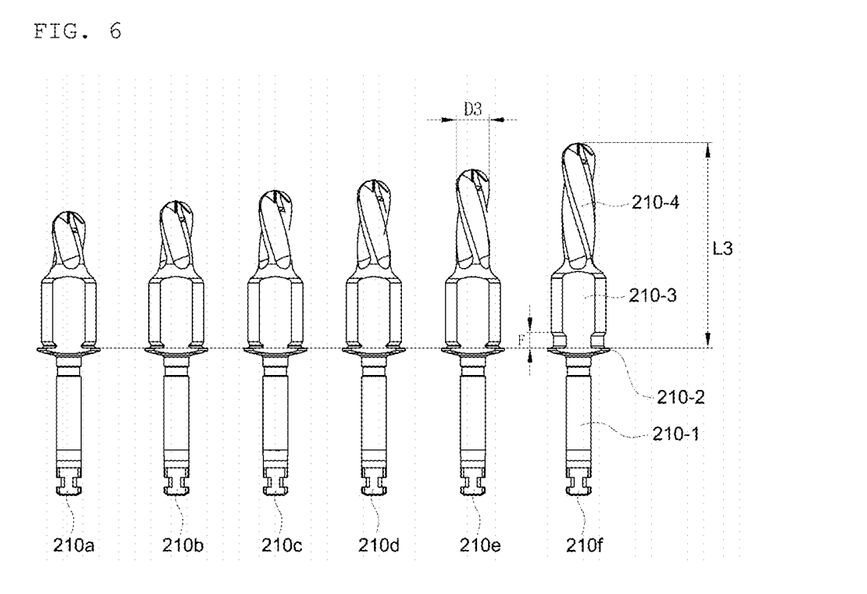
FIG. 6 is a perspective view of sinus drills belonging to a sinus drill group.

FIG. 4 is a perspective view of initial drills for an alveolar bone, which belong to an initial drill group for an alveolar bone, FIG. 5 is a perspective view of dilatation drills for an alveolar bone, which belong to a dilatation drill group for an alveolar bone, and FIG. 6 is a perspective view of sinus drills belonging to a sinus drill group.

Figure 7:
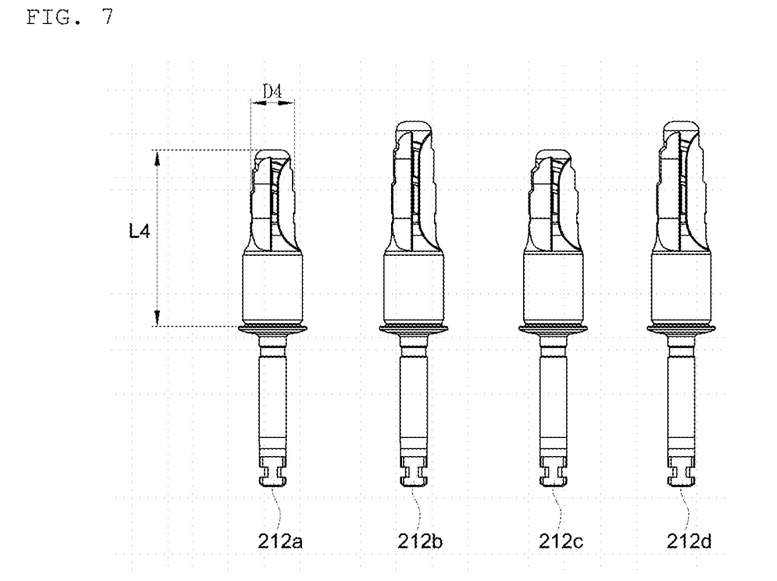
FIG. 7 is a perspective view of final drills belonging to a final drill group.
Figure 8:
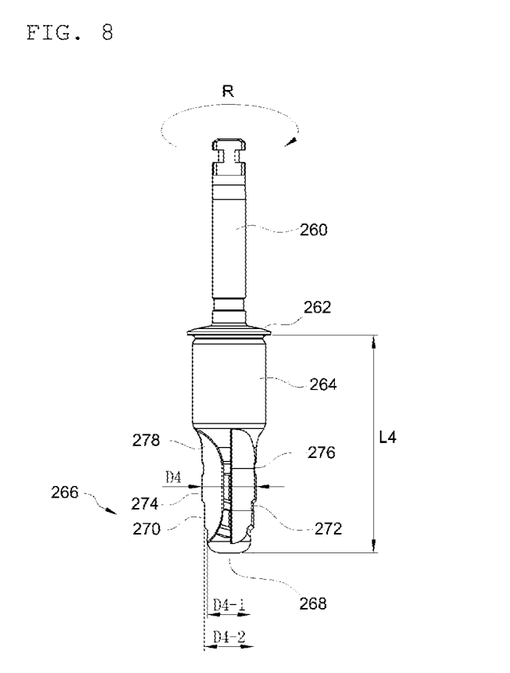
FIG. 8 is a perspective view of a final drill.

FIG. 7 is a perspective view of final drills belonging to a final drill group, and FIG. 8 is a perspective view of a final drill.

Figure 9:
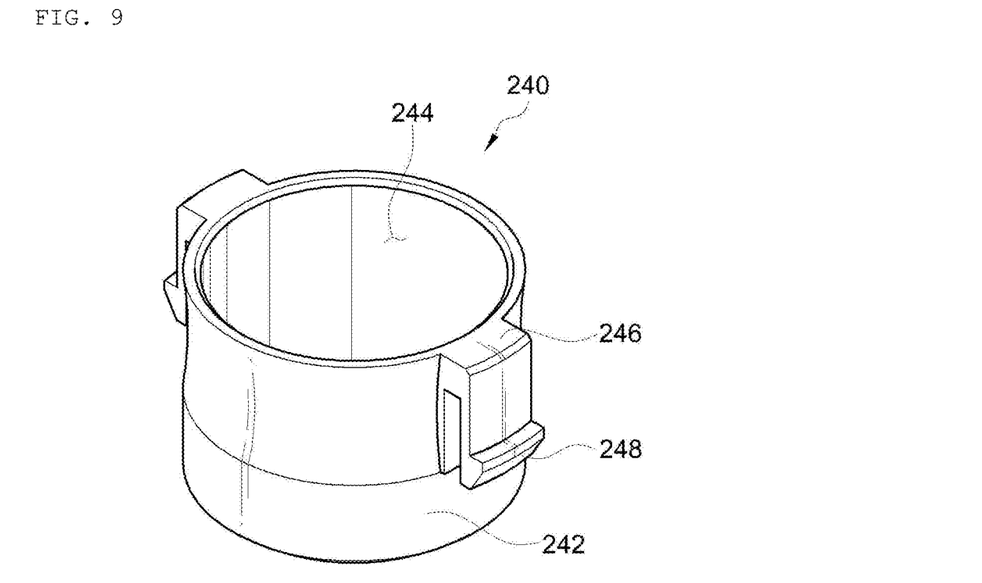
FIG. 9 is a perspective view of a guide bushing.
Figure 10:
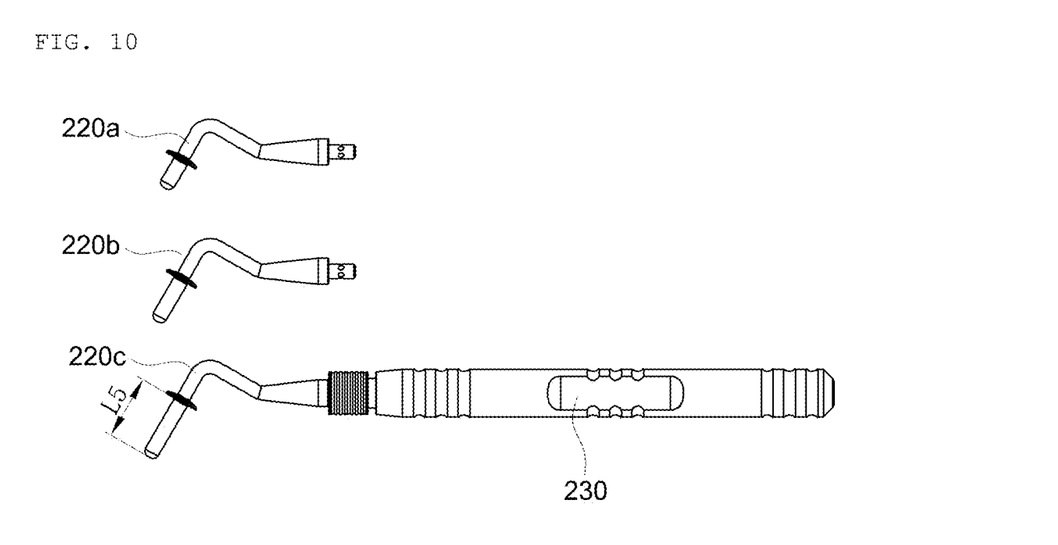
FIG. 10 is a perspective view of bone graft material inserters.
Figure 11:
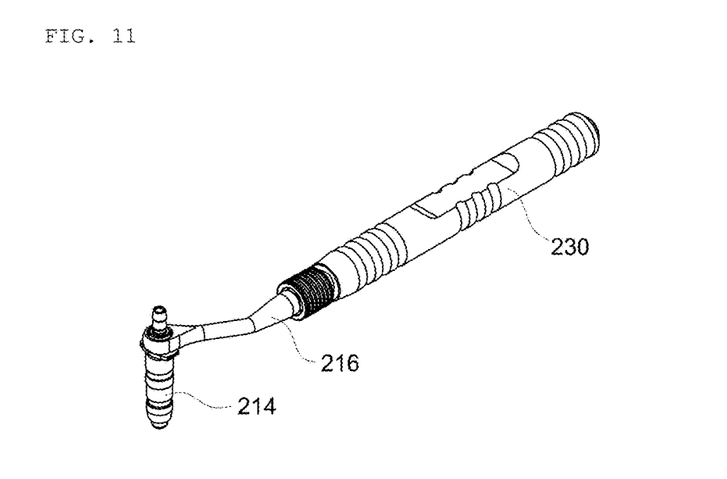
FIG. 11 is a perspective view illustrating a coupling of a sinus elevator to a carrier.

FIG. 9 is a perspective view of a guide bushing, FIG. 10 is a perspective view of bone graft material inserters, and FIG. 11 is a perspective view illustrating a coupling of a sinus elevator to a carrier.

During an implant procedure, when there is not enough bone left to place an implant between the sinus membrane (refer to numeral 14 of FIG. 4) and the alveolar bone (refer to numeral 14 of FIG. 4-12) of a patient, an implant set device for sinus membrane elevation is used to secure a sufficient amount of bone for implant placement by lifting the sinus membrane tissue 14 located above the alveolar bone 12 and filling a space thus made with a bone graft material 16. The implant set device for sinus membrane elevation may consist of a drill group, an associated instrument and a receiving member thereof.

Particularly, an implant set device for sinus membrane elevation may include punch groups 202, 204, drill groups 206 to 212, sinus elevators 214 to 218, a bone graft material inserter group 220, a receiver 110 with regions that can receive a fixture driver 222 and associated instruments 224 to 232, and the above-mention members 202 to 232. An implant set device may further include a guide bushing 240 and a guide stent 250, which are illustrated in FIG. 3, and the receiver 100 may be equipped with additional regions (not shown) storing the guide bushing and the guide stent.

A receiver 100 may include a punch region 102, which can receive a tissue punch 202 and a top drill 204, an initial drill region 104 for an alveolar bone for receiving an initial drill group 206 for an alveolar bone, a dilatation drill region for an alveolar bone 106 for receiving a dilatation drill group 208 for an alveolar bone, a sinus drill region 108 for receiving a sinus drill group 210, and a final drill region 112 that can receive a final drill group 212.

Each region may be equipped with an insertion hole into which a tissue punch 202, drills 204 to 212 and various surgical instruments 214 to 228 are inserted. Each hole may have a rubber receiving portion with consideration for a diameter of an instrument member to be inserted. As a rubber receiving portion is formed by a soft material, an instrument member that is inserted and fixed may be safely received. The instrument member may be fixed for its easy extraction.

Figure 12:
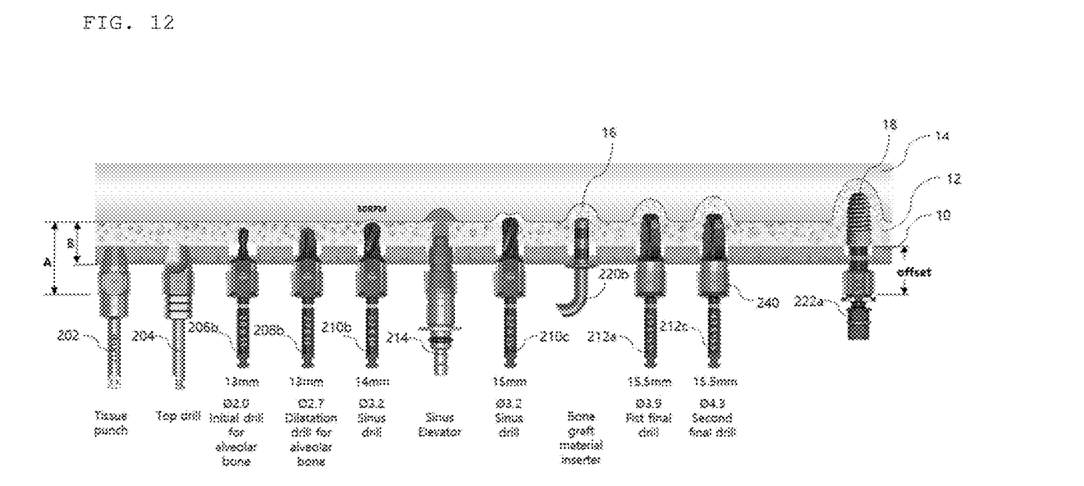
FIG. 12 is a schematic cross-sectional view illustrating a procedure of sinus membrane elevation by members constituting an implant set device for sinus membrane elevation according to an embodiment of the present invention. It may be understood that the appended drawings are not necessarily to scale, presenting a somewhat simplified representation of various features illustrative of the basic principles of the present invention. The specific design features of the present invention as disclosed herein, including, for example, specific dimensions, orientations, locations, and shapes will be determined in part by the particularly intended application and use environment.

Each region 102 to 112 may be set by being extended in a direction exemplified in FIG. 2, that is, in a first direction, a punch region 102, an initial drill region 104 for an alveolar bone, a dilatation drill region 106 for an alveolar bone, a sinus drill region 108 and a final drill region 112 may be sequentially arranged in a second direction, that is, according to a procedure of sinus membrane elevation illustrated in FIG. 12.

In order to sequentially arrange a tissue punch 202 and a top drill 204 from an upper side to a lower side in a first direction within a punch region 102 in compliance with a surgical procedure illustrated in FIG. 12, the punch region 102 may be equipped with insertion holes corresponding to the tissue punch 202 and the top drill 204.

A tissue punch 202 is an instrument used to remove a tissue like gum 10, and a top drill 204 is a cutting drill used for planarization of an irregular surface of an alveolar bone 12 with gum being removed. Alternatively, the top drill 204 is used to remove soft tissue remaining in an alveolar bone 12 after the tissue punch 202.

An initial drill region 104 for an alveolar bone is a portion receiving an initial drill group 206 for an alveolar bone, which consists of initial drills 206a to 206e for an alveolar bone illustrated in FIG. 4. Here, the initial drills 206a to 206e for an alveolar bone form a placement hole by cutting an alveolar bone 12 that is exposed by a top drill 204 or expand a basic placement hole formed in the alveolar bone 12 by the top drill 204. Initial drills 206a to 206e for an alveolar bone perform a drilling by approaching a portion 0.5-1.0 mm away from the sinus membrane 14 illustrated in FIG. 3.

An initial drill group 206 for an alveolar bone includes a multiplicity of initial drills 206a to 206e for an alveolar bone, which have a same effective diameter D1 and an effective length L1 increasing at a first interval.

Each of the initial drills 206a to 206e for an alveolar bone may include a cutting portion 206-4 for forming a placement hole, a guide portion 206-3 that is coupled to the cutting portion 206-4 in order to correspond to a guide hole 254 of a guide stent 250 illustrated in FIG. 3, an engaging portion 206-2 that protrudes from the guide portion 206-3 in the outer diameter direction of the drills 206a to 206e and is thus supported on the upper surface of the guide stent 250 or guide bushing 240, and a coupling portion that is coupled to the engaging portion 206-2 and is mounted on a handpiece (not separately illustrated) giving a rotational force to drills 206a to 206e.

An effective length L1 that is specified in initial drills 206a to 206e for an alveolar bone may be a length adding up a cutting portion 206-4 and a guide portion 206-3, and the length and diameter of each guide portion 206-3 of initial drills 206a to 206e may be set to be equal.

As shown in FIG. 3, an effective length L1 of an initial drill group 206 for an alveolar bone may be set according to a length A from the top of a guide hole 254 of a guide stent 250, which is mounted on gum 10 and guides a drill during an implant surgery including sinus membrane elevation, to the membrane of sinus 14. In FIG. 3, "B" is a length from gum 10 to the membrane of sinus 14, "C" is a residual amount (length) of an alveolar bone 12 identified from a three-dimensional image of mouth for the purpose of judging whether or not to perform a sinus membrane elevation, and "D" is an elevation height of sinus 14 planned by a practitioner.

For example, as shown in Table 1, an effective length L1 of an initial drill group 206 for an alveolar bone increases by 1 mm, which is a first interval, according to the length A. As the body 252 of a guide stent 250 may change during a surgical procedure, the maximum height of a guide hole 254 formed in the body 252 may also change. Accordingly, the number of initial drills 206a to 206e for an alveolar bone, the length of a cutting portion 206-4 and the like may also change. Hence, as a minimum length of the effective length L1 changes, the number and effective length L1 of initial drills 206a to 206e change according to the design specifications of a guide stent 250, thereby not being limited to the numbers and effective lengths provided in Table 1.

embodiment, since both initial drills 206a to 206e for an alveolar bone and drills described below are machined to have the same length and diameter, the above-mentioned inconvenience may be resolved.

In addition, even when a guide bushing 240 is omitted in sinus membrane elevation, a guide hole 254 of a guide stent 250, which is machined to have one length and diameter, is sufficient to correspond to drills that are fabricated to have the same length and diameter. Thus, it is easy to fabricate and use a guide stent 250.

Meanwhile, as initial drills 206a to 206e for an alveolar bone insert different colors for each effective length L1, a practitioner can easily identify an effective length L1. In addition, as a receiver 100 visually marks the same color as the initial drills 206a to 206e corresponding to neighboring insertion holes formed in an initial drill region 104 for an alveolar bone, a practitioner can easily identify an insertion location, while intuitively an initial drill 206a to 206e with a desired effective length L1.

A dilatation drill region 106 for an alveolar bone is a portion that receives a dilatation drill group 208 for an alveolar bone consisting of dilatation drills (or step drills) 208a to 208e for an alveolar bone illustrated in FIG. 5. Here, the dilatation drills 208a to 208e for an alveolar bone dilate a placement hole that is formed in an alveolar bone 12 by an initial drill 206a to 206e for an alveolar bone. Dilatation drills 208a to 208e for an alveolar bone perform a dilatation drilling by approaching a portion 0.5-1.0 mm away from the sinus membrane 14 illustrated in FIG. 3.

A dilatation drill group 208 for an alveolar bone includes a multiplicity of dilatation drills 208a to 208e for an alveolar bone. The dilatation drills 208a to 208e for an alveolar bone consist of a same effective diameter D2, which is larger than

TABLE 1

(Unit: mm)

| Effective length | A (Length from the top of a guide hole of a guide stent to sinus membrane) | | | | | |
|---|---|---|---|---|---|---|
| | 12.2~13.1 | 13.2~14.1 | 14.2~15.1 | 15.2~16.1 | 16.2~17.1 | 17.2~18.1 |
| Initial drill for an alveolar bone (L1) | 12 | 13 | 14 | 15 | 16 | 16 |
| Dilatation drill for an alveolar bone (L2) | 12 | 13 | 14 | 15 | 16 | 16 |
| Sinus drill (L3) | 13 | 14 | 15 | 16 | 17 | 18 |
| First final drill (L4) | | 15.5 | | | 18 | |
| Second final drill (L4) | | 15.5 | | | 18 | |

As shown in FIG. 12, guide portions 206-3 of initial drills 206a to 206e for an alveolar bone may be guided to an alveolar bone 12 through a hole 244 of a guide bushing 240 inserted into a guide hole 254 in some cases, and the initial drills 206a to 206e for an alveolar bone may cut the alveolar bone 12.

In this case, since the guide portions 206-3 of the initial drills 206a to 206e for an alveolar bone have the same length and diameter, the length and diameter of the hole 244 of the guide bushing 240 do not need to be differently prepared, either. In the prior art, since not only initial drills 206a to 206e but also guide portions 208-3, 210-3 and 264 of drills described below are machined to have different lengths and diameters from each other, a multiplicity of guide bushings 240 has to be provided accordingly. However, in this the effective diameter of initial drills 206a to 206e for an alveolar bone, and an effective length L2 that is the same as the effective length of the initial drills 206a to 206e for an alveolar bone belonging to a drill group for surgery in sinus membrane elevation.

A drill group for surgery is a set of drills that are actually used in FIG. 12 illustrating a surgical procedure of sinus membrane elevation. When the form of the guide stent 250 illustrated in FIG. 3 and a mouth structure are taken into consideration, the drill group for surgery means a set of drills from a tissue punch 202, which is to be actually used, to a final drill 212a to 212d, while having an effective length L1 to L4 specified according to a length A from the top of guide stent 250 to the membrane of sinus 14. For example, a drill group for surgery may be drills 206a to 212d with effective lengths L1 to L4 specified in a column of Table 1, where the length A corresponds to 13.2~14.1 mm. In other words, a drill group for surgery may include initial drills 206a to 206e for an alveolar bone, dilatation drills 208a to 208e for an alveolar bone, sinus drills 210a to 201f and the first and second final drills 212a to 212d, which match effective lengths L1 to L4 of each drill when the length A is 13.2~14.1 mm in Table 1.

Each of the dilatation drills 208a to 208e for an alveolar bone may include a cutting portion 208-4, 208-5 for forming a placement hole, a guide portion 208-3, which is coupled to the cutting portion 208-4, 208-5 in order to correspond to a guide hole 254 illustrated in FIG. 3, an engaging portion that protrudes from the guide portion 208-3 in the direction of the outer diameter of drill 208a to 208e and is supported on the upper surface of a guide bushing 240, and a coupling portion 208-1 mounted on a handpiece (not separately illustrated) that is coupled to the engaging portion 208-2 and gives a rotational force to a drill 208a to 208e.

In addition, cutting portions 208-4, 208-5 of dilatation drills 208a to 208e for an alveolar bone may include a lower cutting edge 208-4 and an upper cutting edge 208-5. The lower cutting edge 208-4 has a same effective diameter D2 as a dilatation drill group 208 for an alveolar bone, and the upper cutting edge 208-5 has an effective diameter that is larger than the effective diameter of the lower cutting edge 208-4 and is equal to that L3 of a sinus drill 210a to 210f. In order to prevent the sinus 14 from being damaged by excessive dilatation during initial cutting, a cutting portion 208-4, 208-5 of a dilatation drill 208a to 208e may be formed in a direction where a diameter gradually increases from a lower cutting edge 208-4 to an upper cutting edge 208-5. In addition, in order to make a sinus drill 210a to 210f smoothly enter into a placement hole of an alveolar bone 12 for desired precise drilling during approach to sinus 14 for sinus exposure and to prevent sinus 14 from being damaged by many bone fragments produced by dilatation, it is desirable to machine an upper cutting edge 208-5 with the same effective diameter as the effective diameter of a sinus drill 210a to 210f.

An effective length L2 specified in dilatation drills 208a to 208e for an alveolar bone, like in initial drills 206a to 206e for an alveolar bone, may be a length adding up a cutting portion 208-4, 2085 and a guide portion 208-3. In each of the dilatation drills 208a to 208e for an alveolar bone, the length and diameter of a guide portion 208-3 may be the same and be set to be the same as those of initial drills 206a to 206e for an alveolar bone.

An effective length L2 of a dilatation drill group 208 for an alveolar bone may be set according to a length A from the top of a guide hole 254 to the membrane of sinus 14 and an effective length L1 of an initial drill group 206 for an alveolar bone of a drill group for surgery.

For example, as shown in Table 1, an effective length L2 of a dilatation drill group 208 for an alveolar bone may increase by 1 mm, that is, at a second interval which is the same as a first interval, according to the length A and the effective length L1. However, as the number and effective length L1 of initial drills 206a to 206e change according to the design specifications of a guide stent 250, the numbers and effective lengths provided in Table 1 are not exhaustive.

As shown in FIG. 12, guide portions 208-3 of dilatation drills 208a to 208e for an alveolar bone may be guided to an alveolar bone 12 through a hole 244 of a guide bushing 240 inserted into a guide hole 254 in some cases.

In such a case, since the guide portions 208-3 of dilatation drills 208a to 208e for an alveolar bone have the same length and diameter as initial drills 206a to 206e, the length and diameter of the hole 244 of the guide bushing 240 are not necessary to be differently prepared.

A sinus drill region 108 is a portion that receives a sinus drill group 210 consisting of sinus drills 210a to 210f illustrated in FIG. 6. Here, the sinus drills 210a to 210f precisely cut an alveolar bone 12 adjacent to the membrane of sinus 14 to make an access and opening to the sinus 14, thereby exposing the sinus 14.

A sinus drill group 210 includes a multiplicity of sinus drills 210a to 210e having a same effective diameter D3, which is larger than an effective diameter D2 of dilatation drills 208a to 208e for an alveolar bone, and an effective length L3 which increases at a third interval and is larger than an effective length of dilatation drills 208a to 208e for an alveolar bone.

Like a dilatation drill 208a to 208e for an alveolar bone, each of the sinus drills 210a to 210e may include a cutting portion 210-4, a guide portion 210-3, an engaging portion 210-2 and a coupling portion 210-1. In addition, cutting portions 210-4 of sinus drills 210a to 210e may be uniform from a guide portion 210-3 to a tip, while consisting of a same effective diameter as an upper cutting edge 208-5 of dilatation drill 208a to 208e for an alveolar bone. The cutting portions 210-4 may be equipped with a round shape of peak, while having a lateral cutting edge that is formed until the tip for cutting an alveolar bone 12. This is not only to realize precise cutting of an alveolar bone 12 while a cutting portion 210-4 exposes sinus through a placement hole but also to prevent the sinus 14 from being damaged by sinus 14 opening.

An effective length L3 specified in sinus drills 210a to 210e, like in initial drills 206a to 206e for an alveolar bone, may be a length adding up a cutting portion 210-4 and a guide portion 210-3. In each of the sinus drills 210a to 210e, the length and diameter of a guide portion 208-3 may be the same and be set to be the same as those of initial drills 206a to 206e for an alveolar bone.

An effective length L3 of a sinus drill group 210 may be set according to a length A and an effective length L2 of a dilatation drill group 208 for an alveolar bone of a drill group for surgery.

For example, as shown in Table 1, an effective length L3 of a sinus drill group 210 may increase by 1 mm, that is, at a second interval which is the same as a first interval, according to the length A and the effective length L2. However, as this embodiment assumes a case where the length A is very large, a sinus drill 210f with an effective diameter L3, which has a larger third interval than a sinus drill 210e, may be further added to a sinus drill group 210, and a receiver may also further include an insertion hole receiving the sinus drill 210f in a sinus drill region 108. In addition, as the number and effective length of drills may change according to the design specifications of a guide stent 250, the numbers and effective lengths provided in Table 1 are not exhaustive.

As shown in FIG. 12, guide portions 210-3 of sinus drills 210a to 210e may be guided to an alveolar bone 12 through a hole 244 of a guide bushing 240 inserted into a guide hole 254 in some cases.

In such a case, since the guide portions 210-3 of sinus drills 210a to 210e have the same length and diameter as initial drills 206a to 206e, the length and diameter of the hole 244 of the guide bushing 240 are not necessary to be differently prepared.

Meanwhile, as sinus drills 210a to 210f and dilatation drills 208a to 208e for an alveolar bone insert different colors for each effective length L3 and L2, a practitioner can easily identify effective lengths L2 and L3. In addition, as a receiver 100 visually marks the same color as the initial drills 206a to 206e corresponding to neighboring insertion holes formed in a sinus drill region 108 and a dilatation drill region 106 for an alveolar bone, a practitioner can easily identify an insertion location, while intuitively a drill 208a to 208e with a desired effective length L2 and L3. In order to easily identify an effective length between a drill according to a procedure of sinus membrane elevation and a drill in a drill group for surgery, a color may be marked in the same way in a direction of arranging drills of each drill group, that is, in a second direction of the drill group for surgery.

A final drill region 112 is a portion receiving a final drill group 212 that consists of the first final drills 212a, 212b and the second final drills 212c, 212d, which are illustrated in FIG. 7. Here, as shown in FIG. 12, the first and second final drills 212a to 212d form a hole in a bone graft material implanted between an alveolar bone 12 and sinus 14, before a fixture 18 is placed. Particularly, as shown in FIG. 12, the first final drills 212a, 212b may perform initial drilling for the bone graft material 16, and after the initial drilling, the second final drills 212c, 212d may perform additional drilling for a hole formed in the bone graft material 16, thereby expanding the hole.

A final drill group 212 includes the first final drills 212a, 212b that have a same effective diameter D4, which is larger than a sinus drill 210a to 210e, and an effective length increasing at a fourth interval and are placed in each predetermined section in a drill group for surgery. Like other drill groups in a final drill region 112, the first final drills 212a, 212b are arranged in a first direction, and the second final drills 212c, 212d are arranged in a first direction at the side of the final drills 212a, 212b. In addition, the final drill group 212 may further include the second final drills 212c, 212d, which have a larger effective diameter D4 than the first final drills 212a, 212b and the same effective length L4 as the first final drills 212a, 212b, in each predetermined section of the effective length in a drill group for surgery. In addition, the effective length L4 of the first and second final drills 212a to 212d may be set to be equal to or greater than a maximum effective length of a sinus drill belonging to a predetermined section. The effective length L4 specified in the first and second final drills 212a to 212d may be a length adding up a cutting portion 266 and a guide portion 264. For example, as shown in Table 1, in the predetermined section of 13~15 mm of the effective length L3 of sinus drills 210a to 210e, where the length A corresponds to 12.2~15.1 mm, the first and second final drills 212a to 212d consisting of one effective length L4, which is larger than 15 mm, are allocated.

The effective length L4 of the first and second final drills 212a to 212d may be set according to the length A, the length B and the effective length L3 of a sinus group 210a to 210f of a drill group for surgery.

For example, as shown in Table 1, an effective length L4 of a final drill group 212 may increase by 1.5 mm, that is, at a fourth interval which is larger than a third interval, according to the length A and the effective length L3. The reason why the first and second final drills 212a to 212d have a larger interval of effective length L4 than another drill group 206a to 210f but are smaller in number is that, as a bone graft material 16 with sufficient thickness fills the space between the alveolar bone 12 and the elevated sinus 14, it is not necessary to secure an effective length L4 at a precise interval and the surgery is sufficiently possible even when one first or second final drill 212a to 212e is present in response to a multicity of effective length L3 sections in a sinus drill 210a to 210e. Accordingly, the number of surgical instruments may be reduced.

In this embodiment, there are two first and second final drills 212a to 212d respectively. However, as the number and effective length of drills may change according to the design specifications of a guide stent 250, the numbers and effective lengths provided in Table 1 are not exhaustive.

As shown in FIG. 12, since the first and second final drills 212a to 212d are different only in function and effective diameter D4 according to surgical procedure but actually have the same effective length L4 and shape, the detailed structure of the first final drill 212a will be mainly explained referring to FIG. 8.

The first final drill 212a may include a cutting portion 266 that has a tip portion 268 of non-cutting portion, a guide portion 264 coupled to the cutting portion 266, an engaging portion 262 supported by a guide bushing 240, and a coupling portion 260 connected to a handpiece (not separately illustrated).

The tip portion 268 of the cutting portion 266 is formed as a non-cutting part and has a flat tip surface and rounded edges around the tip surface in order to prevent a neighboring sinus 14 being damaged by cutting a bone graft material 16. The tip portion 268 is machined to have a smaller diameter D4-1 than the effective diameter D3 of a sinus drill 210a to 210l in order to smoothly enter into a placement hole formed by the sinus drill 210a to 210f and prevent the damage of sinus 14 by removing the bone graft material 16 into a flat shape through a strong pressure.

In addition, in sequence toward the tip portion, the cutting portion 266 may be equipped with a multiplicity of cutting edges spaced at a specific angle in the rotational direction (clockwise direction R in FIG. 8) of the first final drill 212a. The cutting edges may include upper and lower cutting edges 274, 270 that are formed in a lateral direction. In addition, the cutting portion may be further equipped with a lower recess 272 and an upper recess 276.

Particularly, in order to easily implement the access of the upper cutting edge 274 by minutely expanding a placement hole that is formed in an alveolar bone 12 by a sinus drill 210a to 210f and also to allow the upper cutting edge 270 to smoothly enter into a space of a bone graft material 16 removed by the tip portion 268 and form a hole, the lower cutting edge 270 may be machined to have a diameter D4-2 that is larger than an effective diameter D3 of a sinus drill 210a to 210f and smaller that an effective diameter D4 of a first final drill 212a.

In order to further expand a hole that is formed by the lower cutting edge 270 from an alveolar bone 12 to a bone graft material 16, the upper cutting edge 274 may be machined to have the same effective diameter as the effective diameter D4 of the first final drill 212a.

A lower recess 272 is placed between a lower cutting edge 270 and an upper cutting edge 274 and may be machined to have a smaller diameter than the diameter D4-2 of the lower cutting edge 270. Hence, cooling water provided during the operation of a first final drill 212a may be induced in the opposite direction to a rotational directing during cutting. In addition, by making bone powder and a bone graft material 16 remain on the outer circumference of the upper cutting edge 274 during rotation, the lower recess 272 contributes to leaving no bone power between cutting edges.

The upper recess 276 is placed on top of the upper cutting edge 274 and may be machined to have a larger diameter than the lower recess 272. Accordingly, in order to induce cooling water in the opposition direction to a rotational direction and to make bone powder and a bone graft material 16 remain in the upper recess 276 when an alveolar bone 12 is cut, the upper recess 276 may be formed in an upward slope in opposition to a rotational direction R.

In addition, a guide portion 264 may be equipped with a curved portion 278 placed between cutting edges of a cutting portion 266. Particularly, seen from a rotational direction R, the curved portion 278 connects the upper parts of a preceding upper cutting edge 276 and a trailing upper cutting edge 276. In this case, in order to make the curved surface of the curved portion 278 placed on top of the preceding upper cutting edge 276 have a gentler slope than a surface placed on top of the trailing upper cutting edge 231, the curved portion may be coupled to the preceding upper cutting edge 276 and the trailing upper cutting edge 276.

Due to the above-mentioned shape of the curved portion 278, since the curved portion 278 is formed to fit the trajectory of cooling water generated by a centrifugal force during rotation along the rotational direction R, a larger amount of cooling water may flow on the top of upper cutting edges 276. Consequently, a cooling range may be maximized.

Meanwhile, the first and second final drills 212a to 212d may be machined to have different effective diameters D4. Alternatively, the tip portions 268 of the first and second final drills 212a to 212d may be machined to have a same diameter D4-1. Accordingly, a second final drill 212c, 212d may enter into a hole, which is formed in a bone graft material 16 by a first final drill 212a, 212b, more easily.

As shown in FIG. 12, guide portions 208-3, 210-3, 264 of dilatation drills 208a to 208e for an alveolar bone, sinus drills 210a to 210e and the first and second final drills 212a to 212d may be guided to an alveolar bone 12 through a hole 244 of a guide bushing 240 inserted into a guide hole 254 in some cases.

In such a case, since the guide portions 208-3, 210-3, 264 of the drills 208a to 212d have the same length and diameter as initial drills 206a to 206e, the length and diameter of the hole 244 of the guide bushing 240 are not necessary to be differently prepared.

A receiver 100 receiving drills 208a to 212d may provide a visually recognizable sign 100 like line in the second direction, where drills of each drill group are arranged, in order to identify a drill according to the procedure of the sinus membrane elevation, and also provide a visually recognizable sign like different colors around an insertion hole in the first direction in order to identify an effective diameter D1 to D4 of a drill belonging to each drill group.

According to the present embodiments, in implant treatment including sinus membrane elevation, a practitioner may easily select a drill suitable for a patient's mouth and alveolar bone, for example, a length A, B diagnosed with a computerized tomographic image for each effective length, while easily identifying a surgical procedure. Especially, as different drills are provided for each effective length, sinus membrane elevation may be performed without auxiliary stopper, thereby preventing the sinus from being damaged.

Meanwhile, a guide bushing 240 illustrated in FIG. 3 and FIG. 9 can be mounted in a guide hole 254 of a guide stent 250. More particularly, while having a shape that closely adhering to the guide hole 254, the guide bushing 240 may include a body 242 with a hole introducing drills 208a to 212d, an extension portion that protrudes outwardly from the body 242 and has elasticity, and an engaging portion 248 that is placed at the end of the extending portion 246 and is coupled to the bottom of the guide body 252 of the guide stent adjacent to the guide hole 254.

Being equipped with the extending portion 246 and the engaging portion 248, the guide bushing 240 can be easily mounted in and removed from the guide hole 254. In addition, as the guide bushing 240 can be fixed while closely adhering to the guide stent 250, it may stably guide drills 206a to 212d and also perform drilling without the drills 206a to 212d being shaken even under vibrations caused by strong rotation.

Referring to FIG. 10, a bone graft material inserter 220a to 220c of a bone graft material group 220 is coupled to a handle 230, infuses a bone graft material between an elevator sinus 14 and an alveolar bone 12 illustrated in FIG. 12, and may be received into a bone graft material inserter region 116 of a receiver 100. As shown in Table 2, a bone graft material inserter 220a to 220c may be provided such that a length B from gum 10 to sinus 14 has one nozzle length L5 in each predetermined section.

TABLE 2

| | (Unit: mm) | | |
|---|---|---|---|
| Nozzle | B (Length from gum to sinus) | | |
| length | 4~7.5 | 7.6~10.5 | 10.6~13.5 |
| Bone graft material inserter (L5) | 6 | 9 | 12 |

Furthermore, as the bone graft material inserters 220a to 220c are distinguished by different colors according to nozzle length L5 and the same color as the bone graft material inserters 220a to 220c are provided around insertion holes of the bone graft material inserter region 116, a practitioner may easily identify and select a suitable bone graft material inserter 220a to 220c according to length B.

Referring to FIG. 11, as an apparatus for sinus membrane elevation that is received in a sinus elevation region 114 of a receiver 100, a sinus elevator 214 is coupled to a carrier 216, thereby being connected to a handle 230. The sinus elevator 214 is coupled to a tube 218 and lifts sinus 14 by a hydraulic pressure of saline solution. As the sinus elevator 214 is mounted on the carrier 216, the carrier contributes to moving the sinus elevator 214 into mouth.

Meanwhile, a receiver 100 may further include a fixture driver region 118 and an auxiliary region 120. The fixture driver region 118 may receive a handpiece type driver 222a and stopper type and non-stopper type drivers 222b, 222c as ratchet type drivers. The auxiliary region 120 may receive an extension adapter 234 extending square type instruments, a drill extension rod 238 for extending a handpiece type handle and a hex driver 236 for screwdriving. If necessary, the receiver 100 may further include a region 122 receiving a handle 230 and another region receiving a torque wrench 232 that rotates a square type driver at a uniform torque.

Hereinafter, referring to FIG. 12, a procedure of sinus membrane elevation using an implant set device for sinus membrane elevation according to an embodiment of the present invention will be described.

FIG. 12 is a schematic cross-sectional view illustrating a procedure of sinus membrane elevation by members constituting an implant set device for sinus membrane elevation according to an embodiment of the present invention. FIG. 12 illustrates a surgical procedure where the length A from the top of a guide hole 254 to the membrane of sinus 14 is diagnosed to be 13.2~14.1 mm and the length B from the gum 10 to the membrane of sinus 14 is diagnosed to be 7.6~10.5 mm. The description below focuses on this case. Lengths A, B may be provided to a practitioner, being judged by a computer tomographic image.

A practitioner draws out a tissue punch 202 and a top drill 204 in the punch region 102 and inserts them into a guide stent 250 along a hole 244 of a guide bushing 240. Then, the practitioner removes tissue like gum 10 and performs cutting to flatten an irregular surface of an alveolar bone 12 with gum being removed.

Next, the practitioner identifies an initial drill 206b for an alveolar bone with an effective length L1 of 13 mm corresponding to the length A by color, draws it out from a receiver 100 and then inserts the same along the hole 244 of the guide bushing 240. After that, the practitioner approaches until a portion 0.5~1.0 mm away from the membrane of sinus 14 and cuts an alveolar bone 12 that is exposed by a top drill 204 in order to form a placement hole or expands a basic placement hole formed in the alveolar bone 12 by the top drill 204.

Next, the practitioner identifies a surgical procedure along a drill group line 110 for surgery and draws out a dilatation drill 208b for an alveolar bone with a length of 13 mm corresponding to the effective length L1 of an initial drill 206b for an alveolar bone by distinguishing the drill 208b through the same color shown in the region of dilatation drill for alveolar bone 106. Next, the practitioner insets the dilatation drill 208b for an alveolar bone by using the guide bushing 240, approaches until a portion 0.5~1.0 mm away from the membrane of sinus 14, and then expands a placement hole that is formed in an alveolar bone 12 by the initial drill 206a for an alveolar drill.

Subsequently, the practitioner identifies a surgical procedure along a drill group line 110 for surgery and draws out a sinus drill 210d with a length of 14 mm corresponding to the effective length L2 of the dilatation drill 208b for an alveolar bone by distinguishing the drill 210b through the same color shown in the sinus drill region 108. Next, the practitioner inserts the sinus drill 201b by the guide bushing 240 and precisely cuts an alveolar bone 12 adjacent to the membrane of sinus 14 to make an access and opening to sinus 14, thereby exposing the sinus 14.

Subsequently, the practitioner lifts the membrane of sinus 14, which is exposed by a hydraulic pressure of saline solution, by using the sinus elevator 214.

Next, the practitioner visually checks a color of the sinus drill region 108, draws out a sinus drill 210c, which is larger by a third interval than the effective length L3 of a sinus drill 210b that is used before the operation of the sinus elevator 214, and then further exposes the sinus 14.

Subsequently, the practitioner identifies a bone graft material inserter 220b, which has a nozzle length corresponding to the length B, by means of color and draws out the inserter 220b. The practitioner infuses a bone graft material between the elevated sinus 14 and the alveolar bone 12. In this case, the guide bushing 240 is skipped, and the bone graft material inserter 220b is inserted through the guide hole 254 of the guide stent 250.

Next, the practitioner identifies a surgical procedure along a drill group line 110 for surgery and draws out a first final drill 212a with an effective length of 15.5 mm corresponding to a section to which the effective length L3 of the sinus drill 210b used prior to the sinus elevator 214 belongs. Next, the practitioner inserts the first final drill 212a by means of the guide bushing 240 and performs initial drilling for a bone graft material 16.

Subsequently, the practitioner identifies a surgical procedure along a drill group line 110 for surgery and draws out a second final drill 212c with an effective length of 15.5 mm corresponding to the effective length L4 of the first final drill 212a and with an effective diameter that is larger than the effective diameter D4 of the first final drill 212a. Next, the practitioner inserts the second final drill 212c by means of the guide bushing 240 and performs additional drilling for a hole from in a bone graft material 16. Thus, the hole may be dilated.

Next, the practitioner places a fixture 18 inside an alveolar bone 12 and a bone graft material 16 by using any one among the handpiece type driver 222a and the ratchet type drivers 222b, 222c. The handpiece type driver is not used for an alveolar bone 12 with high strength and may be used to place a fixture 18 down to a depth of 6.5 mm. In addition, after the handpiece type driver 222a is used to place the fixture 18, the ratchet type drivers 222b, 222c may be used. The ratchet type drivers 222b, 222c are hardly used for a narrow fixture 18.

Although the present invention has been described in detail through the representative embodiments above, it will be understood by those skilled in the art that various modifications can be made without departing from the scope of the present invention with respect to the above-described embodiments. Therefore, the scope of the present invention should not be limited to the embodiments described, but should be defined by all changes or modifications derived from the claims and the equivalent concepts thereto.

What is claimed is:

1. A kit for sinus membrane elevation, the kit comprising:
an initial drill group for an alveolar bone comprising a multiplicity of initial drills, each of the multiplicity of initial drills having a same effective diameter, with respect to each other, and an effective length, the effective length of each of the multiplicity of initial drills increasing in length, with respect to each other, at a first interval;
a dilatation drill group for an alveolar bone comprising a multiplicity of dilatation drills, each of the multiplicity of dilation drills having a same effective diameter, with respect to each other, that is larger than the effective diameter of the initial drills and an effective length, the effective length of each of the multiplicity of dilation drills increasing in length, with respect to each other, at a second interval, such that each effective length of the dilation drills matches each different effective length of the initial drill group;
a sinus drill group comprising a multiplicity of sinus drills, each of the multiplicity of sinus drills having a same effective diameter that is larger than the effective diameter of the dilatation drills and an effective length of each of the multiplicity of sinus drills increasing in length, with respect to each other, at a third interval, wherein the effective lengths of the sinus drills are longer than the effective lengths of the dilatation drills;
a final drill group comprising first final drills for forming a hole in a bone graft material between the alveolar bone and the sinus, the final drills having the same effective diameter with respect to each other, which is larger than the effective diameter of the sinus drills, and an effective length, the effective length of the final drills increasing in length with respect to each other at a fourth interval, the effective lengths of the first final drills being equal or longer than the effective length of one of the sinus drills; and a receiver having a drill region wherein the drills are arranged and received in a first arrangement with the effective length of each drill group increasing in length along a first direction parallel to a column and arranged such that, in a second arrangement, each drill group is arranged along the second direction, parallel to a row.

2. The kit of claim 1, further comprising a guide stent where a guide hole for guiding a drill is formed,
wherein the effective length of the drill group is set according to a length from the top of the guide hole to the membrane of sinus.

3. The kit of claim 2, wherein each of the drills in the drill groups comprises a cutting portion for forming a placement hole, a guide portion that is coupled to the cutting portion to correspond to the guide hole, an engaging portion that protrudes from the guide portion in the direction of the outer diameter of the drill, and a coupling portion for mounting on a handpiece that is coupled to the engaging portion and gives a rotational force to the drill, and
the effective length specified in the drills is a length adding up the cutting portion and the guide portion and, the length and diameter of the guide portion in each of the drills are set to be the same.

4. The kit of claim 2, further comprising a guide bushing that can be mounted in the guide hole of the guide stent in surgical procedure of the sinus membrane elevation,
wherein the guide bushing has a shape that adheres closely to the guide hole and comprises a body with a hole for guiding the drill, an extending portion having elasticity and protruding outwards from the body, and an engaging portion that is placed at the end of the extending portion and is coupled to the bottom of a guide body of the guide stent adjacent to the guide hole.

5. The kit of claim 1, wherein the first interval to the third interval are the same, the fourth interval is set to be larger than the third interval.

6. The kit of claim 1, wherein the first final drills comprise a cutting portion configured to cut the bone graft material and includes a tip portion comprising a non-cutting portion and a guide portion coupled to the cutting portion,
the tip portion comprising the non-cutting portion has a flat tip surface and a rounded edge shape around the tip surface and has a smaller diameter than the effective diameter of the sinus drill, and
the cutting portion comprises a lower lateral cutting edge, which has a larger diameter than the effective diameter of the sinus drill and has a smaller diameter than the effective diameter of the first final drills, an upper lateral cutting edge, which is has the same diameter as the effective diameter of the first final drills, a lower recess that is placed between the lower lateral cutting edge and the upper lateral cutting edge and has a smaller diameter than the diameter of the lower lateral cutting edge, and an upper recess that is placed on the top of the upper lateral cutting edge and has a larger diameter than the diameter of the lower recess.

7. The kit of claim 1, wherein the final drill group further comprises second final drills, which have a larger effective diameter than the first final drills and the same effective length as the first final drills, and
a first tip portion of the first final drills and a second tip portion of the second final drills have the same diameter.

8. The kit of claim 1, further comprising a multiplicity of bone graft material inserters for infusing a bone graft material between an elevated sinus and an alveolar bone,
wherein the receiver further comprises a bone graft material inserter region that may receive the multiplicity of bone graft material inserters.

9. The kit of claim 1, wherein the receiver provides a visually recognizable sign in the second direction, where drills of each drill group are arranged and provides a visually recognizable sign in the first direction in order to identify an effective length of a drill belonging to each drill group.

\* \* \* \* \*